(12) United States Patent
Nissl

(10) Patent No.: US 7,691,142 B2
(45) Date of Patent: Apr. 6, 2010

(54) STENT

(75) Inventor: Thomas Nissl, Garstedt (DE)

(73) Assignee: Qualimed Innovative Medizinprodukte GmbH, Winsen (DE)

( * ) Notice: Subject to any disclaimer, the term of this patent is extended or adjusted under 35 U.S.C. 154(b) by 13 days.

(21) Appl. No.: 10/595,556

(22) PCT Filed: Oct. 11, 2004

(86) PCT No.: PCT/DE2004/002253

§ 371 (c)(1),
(2), (4) Date: Apr. 27, 2006

(87) PCT Pub. No.: WO2005/046522

PCT Pub. Date: May 26, 2005

(65) Prior Publication Data

US 2007/0021823 A1    Jan. 25, 2007

(30) Foreign Application Priority Data

Nov. 10, 2003  (DE) ................................ 103 52 874

(51) Int. Cl.
*A61F 2/06* (2006.01)
(52) U.S. Cl. .................................................. 623/1.15
(58) Field of Classification Search ................ 623/1.15, 623/1.28, 1.17; D24/155
See application file for complete search history.

(56) References Cited

U.S. PATENT DOCUMENTS

| 5,807,404 | A | * | 9/1998 | Richter ....................... 623/1.16 |
| 5,861,027 | A |   | 1/1999 | Trapp |
| 6,217,608 | B1 | * | 4/2001 | Penn et al. .................. 623/1.16 |
| 6,416,539 | B1 | * | 7/2002 | Hassdenteufel ............ 623/1.15 |
| 2003/0105517 | A1 | * | 6/2003 | White et al. ................ 623/1.17 |
| 2004/0002750 | A1 | * | 1/2004 | Majercak ................... 623/1.11 |

FOREIGN PATENT DOCUMENTS

| DE | 295 21 206 U |   | 10/1996 |
| DE | 297 02 671 U |   | 5/1997 |
| DE | 297 16 476 U |   | 12/1997 |
| DE | EP0970664 A2 | * | 1/2000 |
| WO | WO 96/26689 |   | 9/1996 |
| WO | WO 00/32273 A2 |   | 6/2000 |
| WO | WO 01/89417 A1 |   | 11/2001 |
| WO | WO 0189417 A1 | * | 11/2001 |

* cited by examiner

*Primary Examiner*—Todd E Manahan
*Assistant Examiner*—Katherine M Dowe
(74) *Attorney, Agent, or Firm*—Henry M. Feiereisen; Ursula B. Day

(57) ABSTRACT

A stent (1) is a vascular prosthesis for a constricted body vessel. The stent (1) includes a tubular support frame (2) of ring segments (3) arranged in axial succession and formed by struts (5, 6) which in initial state are joined continuously in a wave-like manner. Adjacent ring segments (3) are linked by differently long connectors (9, 10) with U-shaped compensating sections (11, 12). All connectors (9, 10) point in the same circumferential direction (U). Moreover, differently long connectors (9, 10) alternate in circumferential direction (U) as well as in longitudinal stent axis (L).

4 Claims, 2 Drawing Sheets

STENT

CROSS-REFERENCES TO RELATED APPLICATIONS

This application is the National Stage of prior filed copending PCT International application no. PCT/DE2004/002253, filed Oct. 11, 2004, which designated the United States and has been published but not in English as International Publication No. WO 2005/046522, and which claims the priority of German Patent Application, Ser. No. 103 52 874.1, filed Nov. 10, 2003, pursuant to 35 U.S.C. 119(a)-(d).

BACKGROUND OF THE INVENTION

The invention relates to a stent for treatment of stenoses.

Stenoses are innate or acquired vessel blockages or constrictions of tubular body tubes, such as, for example, windpipe, bronchial tubes, esophagus, bile ducts, urinary passages, aorta, and coronary or other body vessels. Stenoses are oftentimes caused by tumors which exert pressure upon the body tubes. Stenoses can be opened by surgical and non-surgical procedures. Non-surgical procedures involve stents which are introduced into the vessel in the area of the stenosis using catheter techniques. The stents assume the function as vascular prostheses for supporting the inner vessel walls.

Stents are available in different constructions and designs of the support frame. WO 96/26689, U.S. Pat. No. 5,861,027 A, DE 297 02 671 U1 or DE 295 21 206 U1 are mentioned here as examples.

The stents include a tubular support frame of metal which is made of several ring segments. The latter are formed by wave-like or meander-shaped struts which are sequentially joined in an endless manner via arcuate sections. Adjacent ring segments in longitudinal axis of the stent are linked by connectors.

Implantation involves compression of the stents, referred to in the art as crimping. When crimped, the stents are transferred with the aid of a suitable instrument into the area of the stenosis and deposited there, wherein the support frame is expandable from an initial state to a support state of comparably greater diameter. This expansion may occur spontaneously, when so-called self-expanding stents are involved, or may be realized with the aid of a suitable tool, a balloon catheter for example.

Practice has shown that the support frames oftentimes are either unable to provide the necessary radial forces to sufficiently resist a stenosis, or are so designed as to impede the function of the vessel. Other constructions, in turn, cannot be sufficiently crimped or are not flexible enough, when crimped, in order to be able to reliably follow the body vessels and its turns.

SUMMARY OF THE INVENTION

Based on the state of art, it is therefore an object of the invention to provide a stent with highest possible stability, in particular radial strength, while allowing good utilization of material.

According to one aspect of the invention, a stent includes a tubular support frame which is expandable from an initial state to a support state. The support frame is made of ring segments which are arranged sequentially in longitudinal stent axis and formed by struts which are joined continuously in a wave-like manner in circumferential direction of the support frame. Adjacent ring segments are linked by differently long connectors with U-shaped compensating sections. All these compensating sections point in accordance with the invention in a same circumferential direction. Connectors of different length alternate in circumferential direction as well as in longitudinal stent axis.

This design is configured in such a manner that in support state of the stent, the immobile struts, which converge respectively with their ends in nodal points that act as friction-free joints, establish a type of self-stabilizing framework structure. Radial forces acting from outside to load the stent are absorbed in the nodal points and deflected there into the various strut directions. Thus, the stent according to the invention is characterized by a high stability and high radial strength. This can be utilized to reduce the material thickness and the strut width of the strut frame, resulting not only in a decrease of material use but in particular in a greater flexibility and better crimping capability of the stent as well as to a better restenosis rate, as existing studies have shown.

The stent may be made of metal. All deformable metals or metal alloys that are medically feasible can be used, e.g. special steel, cobalt alloys (phynox), pure iron, or in particular nickel-titanium alloys.

Of special interest is the stent according to the invention also as plastic stent which generally have no great strength. In particular bio-absorbable plastics are used here.

The stent according to the invention is respectively designed to conform to body vessels of different diameter. A principal configuration in the initial state involves wave-like ring segments and the interposed connectors. The latter are designed geometrically, in particular with respect to length of the diagonal struts and their relative angular disposition, in such a manner that the wave crests on one hand and the wave valleys on the other hand of adjacent ring segments oppose one another frontally.

A characteristic feature of the invention is further that the struts are curved arcuately and merge into one another via arcuate sections, with all struts being curved in the same circumferential direction. This is advantageous for the crimping procedure.

The connectors are placed behind one another in longitudinal stent axis so as to realize a wave-like continuous band of connectors, with short and long connectors changing alternatingly. According to another feature of the present invention, the connections of the connectors, arranged successively in longitudinal stent axis, to the arcuate sections—i.e. in the nodal points—oppose one another frontally. Also this measure positively affects the force pattern in the support frame to resist forces exerted from outside upon the nodal points and deflect them into the struts.

According to another feature of the present invention, the long connectors have arcuate legs which are disposed on both sides of the compensating sections and, in correspondence with the overall design, are curved in the same circumferential direction as the struts.

A length shortening of the support frame, caused theoretically by the expansion process and by the transition of the diagonal struts into a stretched shape, is compensated by the compensating sections in the connectors.

Overall, a frame support is realized with high radial stiffness in the support state. This ensures a very good and homogenous splinting of the vessel wall with a functionally suitable support. Still, a stent according to the invention is very easy to crimp and exhibits in this state a smooth flexible arrangement of the ring segments in the support frame. The stent can very easily be moved through the windings of a body vessel while being arranged on a balloon catheter for example. This smooth handling affords the user and the patient high safety during implantation.

BRIEF DESCRIPTION OF THE INVENTION

An exemplary embodiment of the invention will now be described in more detail with reference to the drawings, in which.

DETAILED DESCRIPTION OF PREFERRED EMBODIMENTS

Figure 1:
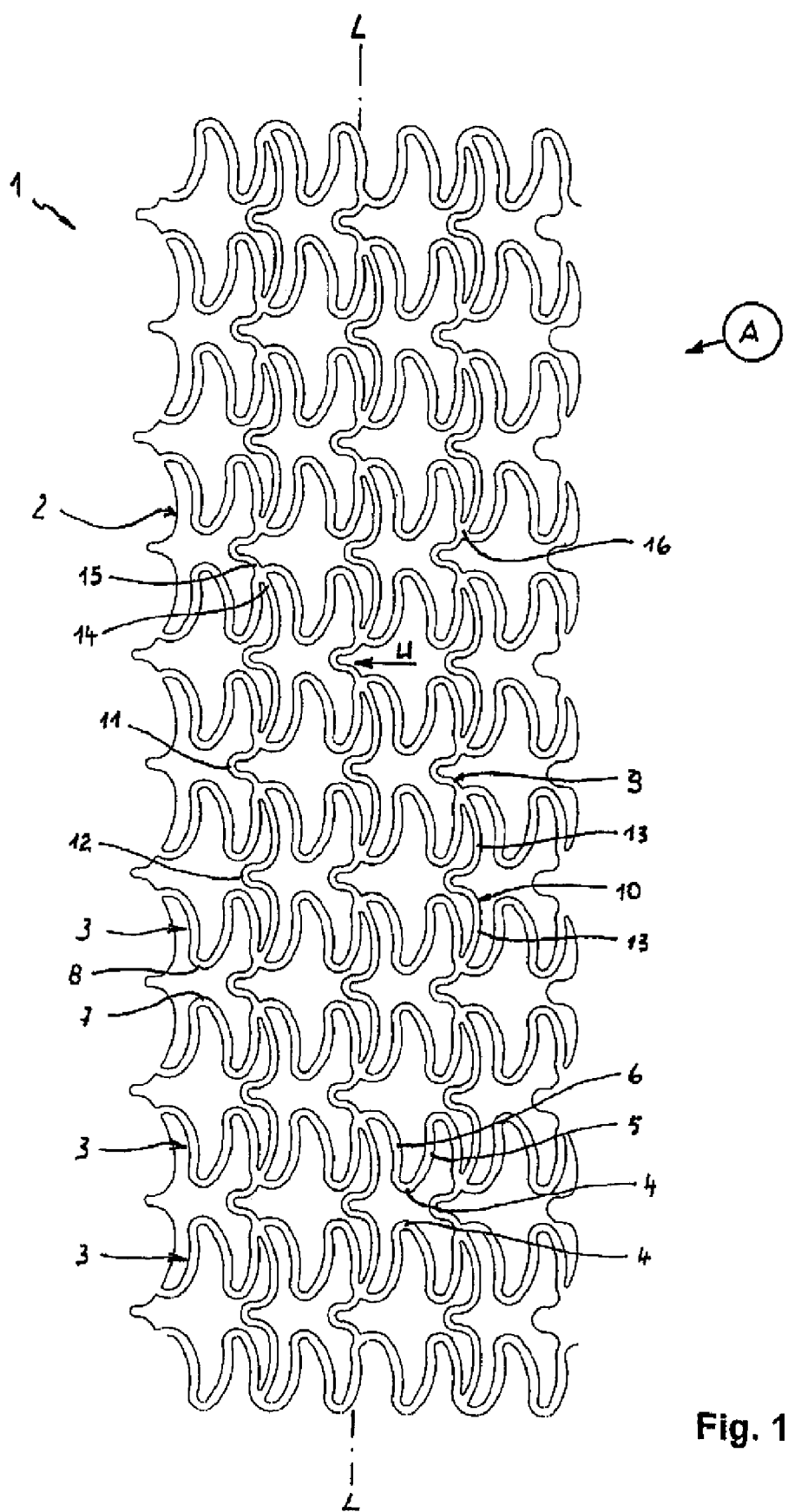
FIG. 1 shows a developed view of the stent pattern of a stent according to the invention in the initial state.
Figure 2:
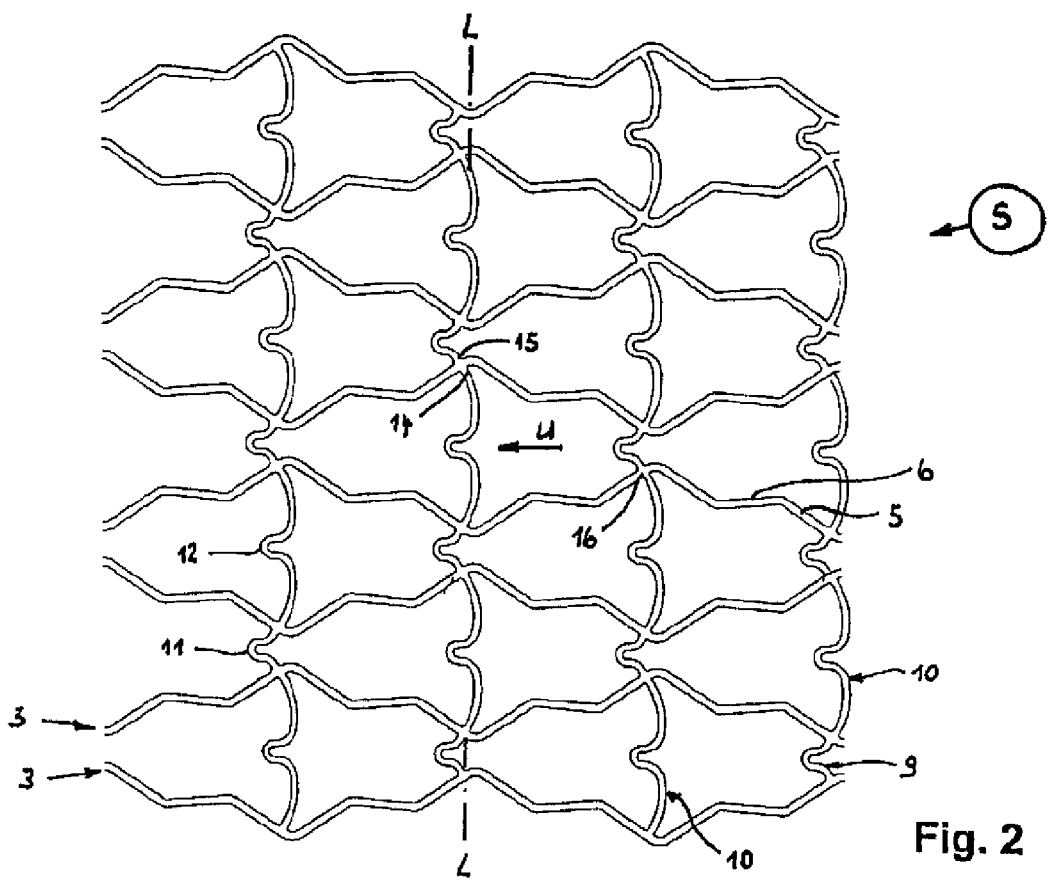
FIG. 2 shows the stent pattern in the support state.

FIGS. 1 and 2 show each a developed view of the stent pattern of a stent 1 according to the invention. FIG. 1 shows the stent pattern of the stent 1 in initial state A after its manufacture. FIG. 2 represents the developed view of the stent pattern in expanded support state S.

The stent 1 is made of metal or plastic and includes a tubular support frame 2 of several ring segments 3 arranged successively behind one another. The illustrations of FIGS. 1 and 2 are not to scale. In particular FIG. 2 does not illustrate the total number of ring segments 3 of the stent 1 as in FIG. 1.

In the non-expanded initial state A, as shown in FIG. 1, the ring segments 3 have a wave-like configuration of struts 5, 6 which continuously adjoin one another via arcuate sections 4. Wave crests 7, on one hand, and wave valleys 8, on the other hand, of adjacent ring segments 3 oppose one another frontally. The rings segments 3 are interconnected by connectors 9, 10 which extend in the direction of the longitudinal stent axis L. Each connector 9, 10 has integrated therein a U-shaped compensating section 11, 12, respectively. The latter point all in a same circumferential direction U across the entire support frame.

It can be seen that the connectors 9 and 10, respectively, are designed of different length. The long connectors 10 have on both sides of the compensating sections 12 arcuate legs 13 which are curved in initial state A in the same circumferential direction U as the struts 5, 6. Short connectors 9 and long connectors 10 alternate in circumferential direction U as well as in longitudinal stent axis L.

Also the struts 5, 6 have an arcuate configuration, with all struts 5, 6 being curved in the same circumferential direction U. The connections 14, 15 of the connectors 9 and 10, respectively, arranged in succession in longitudinal stent axis L, to the arcuate sections 4 oppose one another frontally. As a result, an advantageous force pattern or a force introduction is realized from the nodal points 16 between the struts 5, 6 or the ring segments 3, and the connectors 9, 10.

Figure 3:
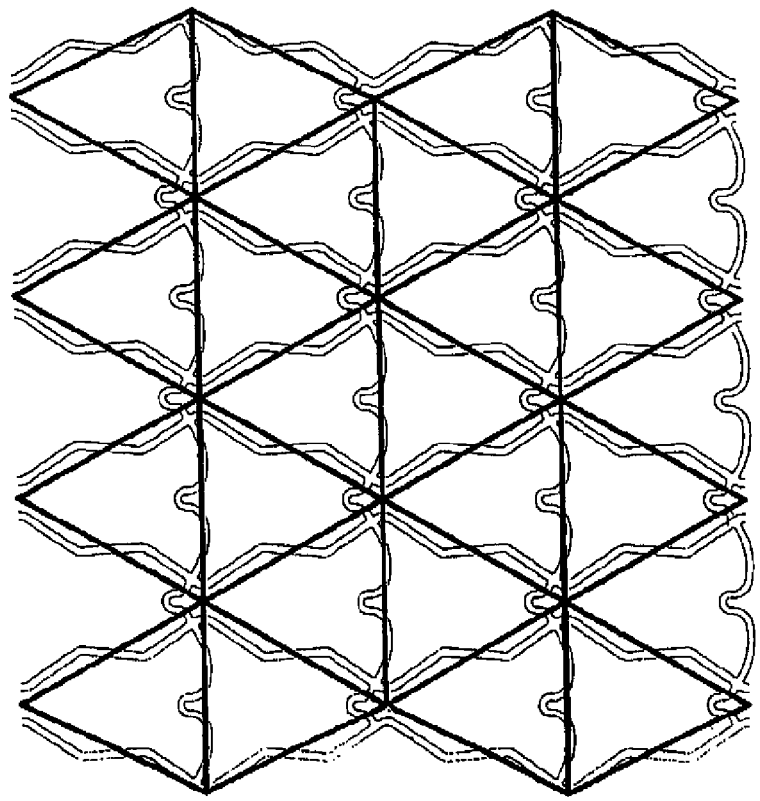
FIG. 3 shows the stent pattern according to FIG. 2 with illustration of the ideally desired framework structure.

The configuration of the support frame 2 results in a self-stabilizing framework structure in the support state S of the stent 1, as shown in FIG. 3 by way of superimposition of a theoretic model upon the support frame 2 in the support state S. The thick line represents the desired ideal framework structure. The immobile struts 5, 6 converge respectively in the nodal points 16, with the nodal points 16 acting like a joint. This configuration ensures a high stability and radial strength in the support state S. In the initial state A, the stent 1 can be curved very easily to a small diameter, and is flexible enough to ensure safe introduction of the stent into a body vessel in the area of a stenosis with the aid of an implantation instrument, normally a balloon catheter. The stent 1 is expanded there. This may take place spontaneously or with the aid of an implantation instrument.

What is claimed is:

1. A stent, comprising a tubular support frame defining a longitudinal axis and expandable from an initial state to a support state, said support frame including a plurality of ring segments arranged in succession in a direction of the longitudinal axis and each formed by struts, which are substantially curved in the initial state in a same circumferential direction and assume a generally linear configuration in the support state, and U-shaped arcuate sections to join the struts to thereby form a wave-like configuration in a circumferential direction of the support frame, wherein adjacent ring segments are linked by first and second connectors which alternate in a same circumferential plane and repeatedly alternate in the direction of the longitudinal axis, wherein successive pairs of first and second connectors are arranged along a substantially same reference line extending in the direction of the longitudinal axis, wherein a pair of first and second connectors connect to a same point on the same one of the U-shaped arcuate sections in opposite relationship to one another in the direction of the longitudinal axis, and wherein each of the first and second connectors is formed with a U-shaped compensating section, with the compensating sections of the first and second connectors pointing in a same circumferential direction, wherein the first connectors have, in a direction of the longitudinal axis, a length which is greater than a length of the second connectors and wherein the first connectors have arcuate legs disposed on both sides of the compensating sections, wherein each of the arcuate legs is disposed in a same circumferential plane adjacent to a corresponding one of the struts and curved in the same circumferential plane as the adjacent strut.

2. The stent of claim 1, wherein the ring segments define wave crests and wave valleys, with the wave crests and wave valleys of adjacent ring segments confronting one another.

3. The stent of claim 1, wherein the connectors, arranged successively in the longitudinal axis are linked to the arcuate sections by connections, with the connections of the first connectors and the connections of the second connectors confronting one another.

4. The stent of claim 1, wherein the first and second connectors substantially retain their configuration, when the tubular support frame expands from the initial state to the support state.

* * * * *